US011267792B2

(12) United States Patent
Raaijmakers et al.

(10) Patent No.: US 11,267,792 B2
(45) Date of Patent: *Mar. 8, 2022

(54) PROCESS TO PREPARE ETHYLENE AMINES AND ETHYLENE AMINE DERIVATIVES

(71) Applicant: NOURYON CHEMICALS INTERNATIONAL B.V., Arnhem (NL)

(72) Inventors: Michiel Jozef Thomas Raaijmakers, Deventer (NL); Antoon Jacob Berend Ten Kate, Arnhem (NL); Rens Veneman, Deventer (NL); Karl Fredrik Lake, Södertälje (SE); Slavisa Jovic, Utrecht (NL); Eike Nicolas Kantzer, Uddevalla (SE); Ina Ehlers, Ödsmål (SE); Rolf Krister Edvinsson, Partille (SE); Björn Patrik Skansen, Mölndal (SE); Michael Bertil Einar Sarning, Gothenburg (SE); Jenny Valborg Therese Adrian Meredith, Årsta (SE); Hendrik Van Dam, Frölunda (SE)

(73) Assignee: NOURYON CHEMICALS INTERNATIONAL B.V., Arnhem (NL)

( * ) Notice: Subject to any disclaimer, the term of this patent is extended or adjusted under 35 U.S.C. 154(b) by 0 days.

This patent is subject to a terminal disclaimer.

(21) Appl. No.: 16/630,291

(22) PCT Filed: Jul. 3, 2018

(86) PCT No.: PCT/EP2018/067868
§ 371 (c)(1),
(2) Date: Jan. 10, 2020

(87) PCT Pub. No.: WO2019/011710
PCT Pub. Date: Jan. 17, 2019

(65) Prior Publication Data
US 2020/0165212 A1    May 28, 2020

(30) Foreign Application Priority Data

Jul. 10, 2017  (EP) .................................. 17180571

(51) Int. Cl.
*C07D 241/04*  (2006.01)
*C07C 213/08*  (2006.01)
*C07D 233/34*  (2006.01)
*C07D 263/22*  (2006.01)
(Continued)

(52) U.S. Cl.
CPC .......... *C07D 241/04* (2013.01); *C07C 213/08* (2013.01); *C07D 233/34* (2013.01); *C07D 233/36* (2013.01); *C07D 263/22* (2013.01); *C07D 413/06* (2013.01)

(58) Field of Classification Search
CPC .... C07D 233/36; C07D 233/34; C07C 209/16
See application file for complete search history.

(56) References Cited

U.S. PATENT DOCUMENTS 2,812,333 A  11/1957  Steele
3,133,932 A   5/1964  Horn et al.
4,387,249 A   6/1983  Harnden et al.
(Continued)

FOREIGN PATENT DOCUMENTS

EP   0222934 A1   5/1987
EP   1654214 B1   3/2007
(Continued)

OTHER PUBLICATIONS

ISA, European Patent Office, International Search Report and Written Opinion issued in International Application No. PCT/EP2018/067866, dated Sep. 14, 2018.
ISA, European Patent Office, International Search Report and Written Opinion issued in International Application No. PCT/EP2018/067867, dated Aug. 20, 2018.
ISA, European Patent Office, International Search Report and Written Opinion issued in International Application No. PCT/EP2018/067868, dated Oct. 1, 2018.
ISA, European Patent Office, International Search Report and Written Opinion issued in International Application No. PCT/EP2018/067869, dated Sep. 14, 2018.
EPO, European Extended Search Report issued in European Patent Application No. 17180568.2, dated Oct. 13, 2017.
EPO, European Extended Search Report issued in European Patent Application No. 17180569.0, dated Jan. 22, 2018.
(Continued)

Primary Examiner — Daniel R Carcanague
(74) Attorney, Agent, or Firm — Lorenz & Kopf, LLP

(57) ABSTRACT

A process is provided for preparing ethyleneamines of the formula $NH_2-(C_2H_4-NH-)_pH$ wherein p is at least 3, or derivatives thereof wherein one or more units $-NH-C_2H_4-NH-$ may be present as a cyclic ethylene urea unit or piperazine unit or between two units $-NH-C_2H_4-NH-$ a carbonyl moiety is present. The process includes reacting an ethanolamine-functional compound $OH-(C_2H_4-NH-)_qH$ wherein q is at least 2, an amine-functional compound $NH_2-(C_2H_4-NH-)_rH$ wherein r is at least 1, in the presence of a carbon oxide delivering agent, wherein the molar ratio of ethanolamine-functional compound to amine-functional compound is from about 0.05:1 to about 0.7:1 and the molar ratio of carbon oxide delivering agent to amine-functional compound is higher than the molar ratio of ethanolamine-functional compound to amine-functional compound, provided that the process does not comprise reacting 3 moles of ethylenediamine (EDA) and 1 mole of AEEA (aminoethylethanolamine) in the presence of 1.65 moles of urea at 280 deg C. for 2 hours.

18 Claims, No Drawings

(51) Int. Cl.
*C07D 413/06* (2006.01)
*C07D 233/36* (2006.01)

(56) References Cited

U.S. PATENT DOCUMENTS

| | | | |
|---|---|---|---|
| 4,503,250 A | 3/1985 | Herdle | |
| 4,568,745 A | 2/1986 | Ghelli et al. | |
| 5,262,534 A | 11/1993 | King | |
| 5,364,971 A | 11/1994 | Su | |
| 5,491,263 A | 2/1996 | Rooney et al. | |
| 10,428,010 B2 * | 10/2019 | Edvinsson | C07D 233/36 |
| 10,428,011 B2 * | 10/2019 | Edvinsson | C07C 269/06 |
| 10,793,511 B2 * | 10/2020 | Ten Kate | C07C 213/02 |
| 10,800,731 B2 * | 10/2020 | Veneman | C07D 263/20 |
| 10,844,001 B2 * | 11/2020 | Edvinsson | C07C 273/1809 |
| 10,975,017 B2 * | 4/2021 | Kantzer | C07C 209/62 |
| 10,995,058 B2 * | 5/2021 | Kantzer | C07D 233/32 |
| 10,995,077 B2 * | 5/2021 | Edvinsson | C07D 295/13 |
| 2007/0043217 A1 | 2/2007 | Siegert et al. | |
| 2007/0100144 A1 | 5/2007 | Frauenkron et al. | |
| 2010/0029976 A1 | 2/2010 | Dahmen et al. | |
| 2010/0087681 A1 | 4/2010 | Petraitis et al. | |
| 2010/0087683 A1 | 4/2010 | Cook et al. | |
| 2010/0120983 A1 | 5/2010 | Dufaure et al. | |
| 2019/0031597 A1 * | 1/2019 | Edvinsson | C07C 273/1809 |
| 2019/0039993 A1 * | 2/2019 | Edvinsson | C07C 275/14 |
| 2019/0047971 A1 * | 2/2019 | Edvinsson | C07D 295/13 |
| 2020/0131136 A1 * | 4/2020 | Ten Kate | C07C 209/16 |
| 2020/0165187 A1 * | 5/2020 | Ten Kate | C07C 209/86 |
| 2020/0165207 A1 * | 5/2020 | Kantzer | C07C 209/78 |
| 2020/0199060 A1 * | 6/2020 | Ten Kate | C07C 209/62 |
| 2020/0199077 A1 * | 6/2020 | Veneman | C07D 295/03 |
| 2020/0207701 A1 * | 7/2020 | Veneman | C07D 233/36 |
| 2020/0223785 A1 * | 7/2020 | Raaijmakers | C07C 209/62 |
| 2020/0223800 A1 * | 7/2020 | Ten Kate | C07D 233/34 |
| 2020/0361850 A1 * | 11/2020 | Kantzer | C07C 213/02 |
| 2020/0361851 A1 * | 11/2020 | Veneman | C07C 209/86 |
| 2020/0361852 A1 * | 11/2020 | Ten Kate | C07C 213/02 |
| 2020/0361873 A1 * | 11/2020 | Van Dam | C07C 209/70 |
| 2020/0361910 A1 * | 11/2020 | Ehlers | C07D 295/125 |
| 2020/0362111 A1 * | 11/2020 | Veneman | C08G 73/0213 |

FOREIGN PATENT DOCUMENTS

| | | | |
|---|---|---|---|
| EP | 2548869 A1 | 1/2013 | |
| FR | 2912148 | 8/2008 | |
| GB | 1510538 | 5/1978 | |
| TW | 200520830 A | 7/2005 | |
| WO | 9749686 A1 | 12/1997 | |
| WO | 2011079008 A1 | 6/2011 | |
| WO | 2011107512 A1 | 9/2011 | |
| WO | 2017137529 A1 | 8/2017 | |
| WO | 2017137530 A1 | 8/2017 | |
| WO | 2017137532 A1 | 8/2017 | |
| WO | WO-2017137531 A1 * | 8/2017 | C07C 269/06 |
| WO | WO-2018215326 A1 * | 11/2018 | C07D 233/36 |
| WO | WO-2020165330 A1 * | 8/2020 | C07C 209/16 |

OTHER PUBLICATIONS

EPO, European Extended Search Report issued in European Patent Application No. 17180571.6, dated Jan. 22, 2018.
EPO, European Extended Search Report issued in European Patent Application No. 17180573.2, dated Jan. 22, 2018.

* cited by examiner

PROCESS TO PREPARE ETHYLENE AMINES AND ETHYLENE AMINE DERIVATIVES

CROSS-REFERENCE TO RELATED APPLICATION

This application is a U.S. National-Stage entry under 35 U.S.C. § 371 based on International Application No. PCT/EP2018/067868, filed Jul. 3, 2018, which was published under PCT Article 21(2) and which claims priority to European Application No. 17180571.6, filed Jul. 10, 2017, which are all hereby incorporated in their entirety by reference.

TECHNICAL FIELD

The present invention relates to a process for making higher ethylene amines (EA), i.e. ethylene amines and derivatives (or precursors) thereof, like urea derivatives, that contain at least 3 ethylene units, by reacting an ethanolamine functional compound containing at least 2 ethylene units with an amine functional compound in the presence of a carbon oxide delivering agent.

BACKGROUND

Ethylene amines consist of two or more nitrogen atoms linked by ethylene units. Ethylene amines can be present in the form of linear chains $H_2N(-C_2H_4NH)_p-H$. For p=1, 2, 3, 4, . . . these are denoted EDA, DETA, L-TETA, L-TEPA, . . . .

With three or more ethylene units it is also possible to create branched ethylene amines such as $N(CH_2CH_2NH_2)_3$, TAEA. Two adjacent nitrogen atoms linked by two ethylene units are called a piperazine ring

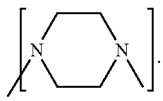

Piperazine rings can be present in longer chains to produce the corresponding cyclic ethylene amines.

Two adjacent nitrogen atoms linked by one ethylene unit and one carbonyl moiety form a cyclic ethylene urea (EU). An ethylene amine (EA) in which two nitrogen atoms are linked intramolecular by a carbonyl moiety

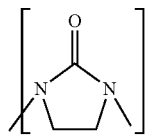

is here referred to as an UEA. Replacing the carbonyl bridge with two hydrogen atoms yields the corresponding ethylene amine. For example: EU↔EDA, UDETA↔DETA, UAEEA↔AEEA, UTETA↔L-TETA, UTEPA↔L-TEPA. Some higher amines host more than one carbonyl moiety, e.g. DUTETA the diurea of L-TETA. The carbonyl moiety may link nitrogen atoms on two separate molecules. For example $H_2NC_2H_4NH-CO-NHC_2H_4NH_2$ and replacing the carbonyl moiety with two hydrogen atoms here yields two EDA.

Each amine function in ethylene amines and ethylene ureas can be primary, secondary or tertiary. Furthermore, a secondary amine can be linear (linear secondary amines, LSA) or cyclic (cyclic secondary amine, CSA).

In the presence of any Brønsted acid (such as water) ethylene amines (EA) can be protonated ($EAH^+$). If not otherwise stated the term amine in this document will include both the protonated and unprotonated form.

Some ethylene amines and urea derivatives thereof are shown below as an illustration. This can naturally be extended to include a.o. pentaamines, hexaamines and so on.

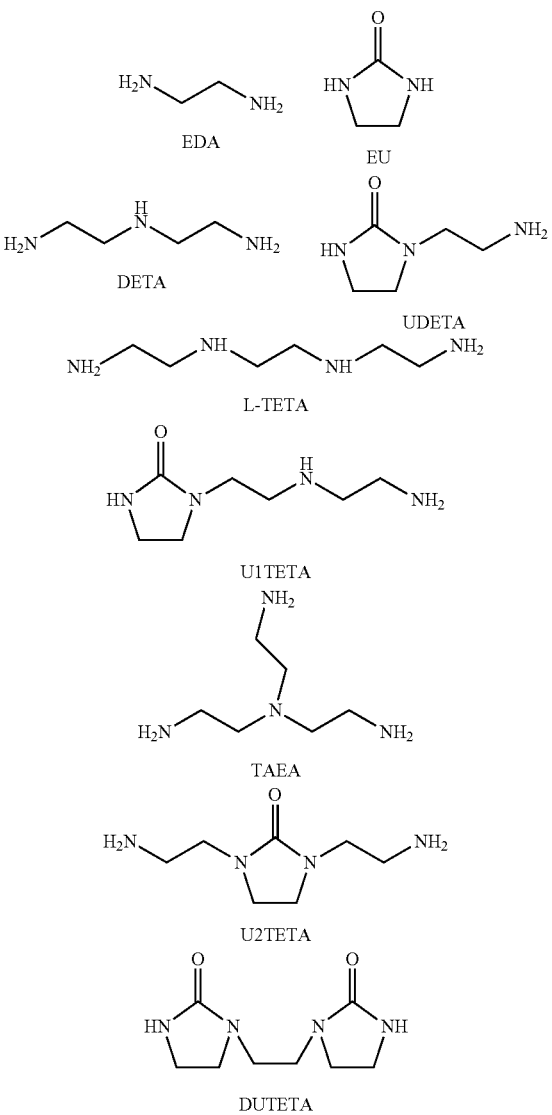

As to naming of the molecules, EDA stands for ethylenediamine, DETA for diethylenetriamine, TETA for triethylenetetraamine, TEPA for tetraethylenepentamine, PEHA for pentaethylenehexamine. When there is a single cyclic urea in the molecule this is indicated by adding a U in front of the name, i.e. UTETA means the cyclic urea of TETA, while when there are two cyclic ureas in the molecule this is indicated by DU, i.e. DUTETA means the cyclic diurea of TETA. If there is a number indicated for the U this refers to the amino group where the U group is located. There is one exception to this naming and that is that instead of UEDA the abbreviation EU is used, which stands for ethyleneurea. Furthermore, TAEA stands for trisaminoethylamine.

The manufacturing of ethylene amines is presently dominated by two routes. These are the reductive amination of MEA and the EDC route.

Reductive amination of MEA proceeds in the presence of a hydrogenation/dehydrogenation catalyst in an excess of ammonia. Next to the reductive amination of MEA to give EDA a number of side reactions including transamination produce a mixture of a large number of ethylene and ethanolamines. The output is dominated by mono and diethylene products (EDA, DETA, PIP and AEEA). Higher ethylene and ethanolamines are also formed but the mixture is complex and ineffective in producing high yields of the most important higher ethylene amines TETA and TEPA.

Several attempts to use transamination to produce ethylene amines with two or more ethylene units have been reported but seem limited to the diethylene compound DETA and have not been competitive to the EDC route described further below. See for example U.S. Pat. No. 8,383,860 B2; U.S. Pat. No. 8,188,318 B2; EP1654214B1 and U.S. Pat. No. 4,568,745.

The EDC route is the substitution reaction of EDC (ethylene dichloride) with ammonia and/or another ethylene amine at elevated temperatures and pressures to form hydrochlorides which are then reacted with caustic to generate mixtures of ethylene amines and NaCl.

Today, the EDC-based process is the main process for producing higher polyethylene polyamines. By higher ethylene amines we refer to those containing three or more ethylene units. AEP is an example of a triamine. Higher amines usually exist in so-called technical mixtures. For example, there are several tetramines possible and their technical mixture which is referred to as TETA typically comprises L-TETA, TAEA, DAEP, PEEDA. Similarly TEPA refers to a mixture of pentaamines (linear, branched and piperazine containing).

The EDC route apart from it being fully dependent on the use of ethylene dichloride which is toxic, highly flammable and carcinogenic, expensive, difficult to handle and therefore not always and everywhere available has as a disadvantage that it has a low selectivity towards specific higher ethylene amines, as it gives a mixture of many different polyethylene amines. Furthermore the EDC route results in the creation of a lot of NaCl which in embodiment results in corrosion and colored products thereby creating a need for additional purification steps like distillation or bleaching.

U.S. Pat. No. 5,262,534 discloses a process for N,N,N trisubstituted nitrogen-containing compounds, for example by reacting a piperazine with a CO2 synthon, such as certain oxazolidinones. Because oxazolidinones are a carbonic acid derivative of an ethanolamine, in all examples in the document the relative amount of carbonic acid derivative to ethylene amine is the same as the relative amount of ethanolamine to ethylene amine.

U.S. Pat. No. 4,503,250 discloses the preparation of linear triethylene tetraamine L-TETA by reacting aminoethylethanolamine (AEEA) with EDA and a carbonic acid derivative (i.e. a carbon oxide delivering agent). It is said that the carbonic acid derivative can be a compound formed by earlier addition of an amine or alcohol to carbon dioxide. Though the document states in general that the components may be used in any amount, it suggests that the carbonic acid derivative functions as a catalyst and in all examples the carbonic acid derivative is used in a small amount relative to ethylene amine compound never to exceed the relative amount of ethanolamine to ethyleneamine compound. In the Examples, entry 5, AEEA is reacted with imidazolidinone (i.e a carbonic acid derivative of EDA) to give L-TETA, however in this Example the amount of carbon oxide delivering agent is very low, only around 0.3 equivalent on total amine compound (i.e. total EDA present in the imidazolidinone and as EDA) similarly low as the amount of ethanolamine-functional compound on amine-functional compound which is also 0.3 equivalent. For some embodiments it is indicated that the product mixture was only obtained after hydrolysis.

In pending PCT patent application PCT/EP2017/052948 a process is disclosed to prepare ethyleneamines of the formula NH2-(C2H4-NH—)pH wherein p is at least 3 or derivatives thereof wherein one or more units —NH-C2H4-NH— may be present as a cyclic ethylene urea unit or between two units —NH-C2H4-NH— a carbonyl moiety may be present, by reacting an ethanolamine-functional compound, an amine-functional compound in the presence of a carbon oxide delivering agent, wherein the molar ratio of ethanolamine-functional compound to amine-functional compound is at least 0.7:1 and the molar ratio of carbon oxide delivering agent to amine-functional compound is at least 0.05:1. This document focuses at maximizing yield of ethyleneamines product. In a comparative Example 2 in this document the reaction of 3 moles EDA, 1 mole AEEA and 1.65 moles of urea at 280 deg C. for 2 hours is disclosed, which reaction is disclaimed in this application, even though the selectivity in this reaction was not determined.

BRIEF SUMMARY

A process is provided for preparing ethyleneamines of the formula $NH_2$—$(C_2H_4$—$NH$—$)_p$H wherein p is at least 3, or derivatives thereof wherein one or more units —NH—$C_2H_4$—NH— may be present as a cyclic ethylene urea unit

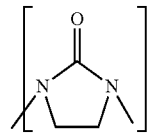

or piperazine unit

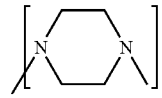

or between two units —NH—$C_2H_4$—NH— a carbonyl moiety is present. The process includes reacting an ethanolamine-functional compound OH—$(C_2H_4$—NH—$)_q$H wherein q is at least 2, an amine-functional compound $NH_2$—$(C_2H_4$—NH—$)_r$H wherein r is at least 1, in the presence of a carbon oxide delivering agent, wherein the molar ratio of ethanolamine-functional compound to amine-functional compound is from about 0.05:1 to about 0.7:1 and the molar ratio of carbon oxide delivering agent to amine-functional compound is higher than the molar ratio of ethanolamine-functional compound to amine-functional compound, provided that the process does not comprise reacting 3 moles of ethylenediamine (EDA) and 1 mole of AEEA (aminoethylethanolamine) in the presence of 1.65 moles of urea at 280 deg C. for 2 hours.

DETAILED DESCRIPTION

It has now been found that selectivity of the process to the ethylene amines products can be improved if the ratio ethanolamine-functional compound:amine-functional compound is relatively low and the carbon oxide delivering agent is dosed in a higher amount on amine-functional compound than the ethanolamine compound.

The selectivity of the process for the purpose of this application is defined as the molar selectivity of the ethanolamine reactant and/or its carbamate or urea derivative towards the higher ethyleneamines as prepared in the process (of the formula NH2-(C2H4-NH—)pH wherein p is at least 3 or derivatives thereof wherein one or more units —NH-C2H4-NH— may be present as a cyclic ethylene urea unit or between two units —NH-C2H4-NH— a carbonyl moiety may be present). The selectivity can be calculated from the moles of higher ethyleneamines formed per mole of ethanolamine converted with respect to the ethanolamine used as a raw material in the process.

Even though the yield is not as high as possible such a process is very advantageous as much fewer side products are formed and unreacted starting materials can be easily recycled The present invention now provides a process to prepare ethyleneamines of the formula NH2-(C2H4-NH-)pH wherein p is at least 3, or derivatives thereof wherein one or more units —NH—C$_2$H$_4$—NH— may be present as a cyclic ethylene urea unit

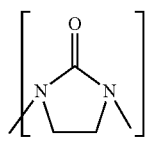

or piperazine unit

or between two units —NH—C$_2$H$_4$—NH— a carbonyl moiety is present, by reacting an ethanolamine-functional compound OH—(C$_2$H$_4$—NH—)$_q$H wherein q is at least 2, an amine-functional compound NH$_2$—(C$_2$H$_4$—NH—)$_r$H wherein r is at least 1 in the presence of a carbon oxide delivering agent, wherein the molar ratio of ethanolamine-functional compound to amine-functional compound is between 0.05:1 and 0.7:1 and the molar ratio of carbon oxide delivering agent to amine-functional compound is higher than the molar ratio of ethanolamine-functional compound to amine-functional compound, provided that the process is not the process of reacting 3 moles ethylenediamine (EDA) and 1 mole AEEA (aminoethylethanolamine) in the presence of 1.65 moles of urea at 280 deg C. for 2 hours.

It was found that the selectivity of the reaction towards producing specific higher ethylene amines increases when working within the molar ratio ranges of the present invention, wherein the selectively obtained specific higher ethyleneamine product is the product wherein the value of p is the sum of q and r, including its urea derivatives.

It should be noted that U.S. Pat. No. 4,387,249 discloses a selective process to manufacture diethylene triamine by reacting monoethanolamine, ethylenediamine and urea. The document says that the most preferred mole ratio of the reactants ethylenediamine to urea to ethanolamine is about 3/1.25/1. Monoethanolamine is an ethanolamine-functional compound OH—(C2H4-NH-)qH wherein q is 1 and thereby outside the scope of the present invention. Also monoethanolamine is in reactions as the one covered by the present invention not comparable with the ethanolamines wherein q is at least 2 due to the propensity of monoethanolamine to form a carbamate rather than a urea which is the case for ethanolamines where q is 2 or higher. For example, contacting a carbon oxide delivering agent with monoethanolamine and aminoethylethanolamine, respectively, at a suitable reaction temperature will produce CMEA and UAEEA, respectively, as can be found in U.S. Pat. No. 3,133,932 that discloses the formation of the cyclic MEA-derived carbamate CMEA and in WO97/49686 that discloses in Example L the formation of the cyclic AEEA-derived urea UAEEA. The former is a cyclic carbamate and the latter is a cyclic urea and they display substantially different chemical reactivities and hence kinetic and thermodynamic profiles as intermediates such as in the present invention. As a skilled person will understand, the reactivity of the separate reactants largely influences the selectivity towards such reactants. All the above makes that the reaction as found for monoethanolamine does not have predictive value for how bigger ethanolamines will react. This can also be seen below where the optimum for the ratio of carbon oxide delivering agent to other reactants is given. This clearly deviates from the optimum defined in U.S. Pat. No. 4,387,249 for using MEA.

Preferably, the molar ratio of carbon oxide delivering agent to amine-functional compound is at least 10% higher than the molar ratio of ethanolamine-functional compound to amine-functional compound. In a more preferred embodiment the molar ratio of carbon oxide delivering agent to amine-functional compound is at least 20% higher than the molar ratio of ethanolamine-functional compound to amine-functional compound. In even more preferred embodiments when starting from amines and ethanolamines that are bigger in size and that contain 3 or more ethylene units, the molar ratio of carbon oxide delivering agent to amine-functional compound is at least 50% higher than the molar ratio of ethanolamine-functional compound to amine-functional compound. The molar ratio of carbon oxide delivering agent to amine-functional compound in embodiments can be up to 500% higher than the molar ratio of ethanolamine-functional compound to amine-functional compound, but preferably is up to 300% higher, even more preferably 200% higher. In another preferred embodiment the molar ratio of ethanolamine-functional compound to amine-functional compound is between 0.1:1 and 0.5:1, even more preferably between 0.2:1 and 0.4:1.

It should be noted that compounds exist that contain more than one carbonyl group that can be released from the molecule for transfer to the ethanolamine-functional compound, such as for example DUTETA. When determining the molar ratio for such compounds there should be an adjustment for the molar amount of carbon oxide they can release for transfer to the ethanolamine-functional compound. Accordingly, 1 mole of DUTETA should be considered 2 moles of carbon oxide delivering agent.

The molar amount of carbon oxide delivering agent on amine-functional compound is determined by the reactants in the process, independent of the dosing regime used for the reactants.

The reaction mixture is characterized by containing as reactants ethanolamine-functional compound, amine-functional compound and carbon oxide delivering agent and can be roughly represented by below non-limiting scheme.

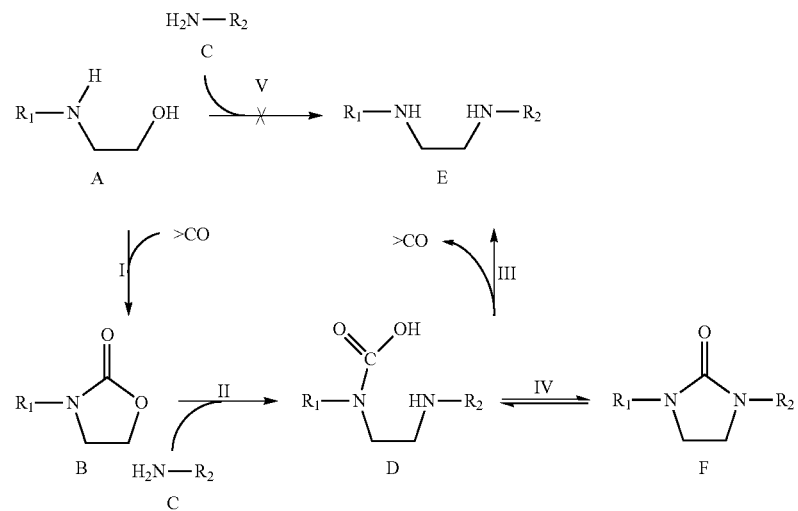

I  Addition of CO to the ethanolamine to form the 2-oxazolidinone ring
II  Chain extension by ring opening by primary amine
III  Removal of carbonyl group to form the ethylene amine
IV  Intramolecular rearrangement of carbonyl group
V  Hypothetical direct uncatalyzed amination A number of reactions take place in parallel when heating a mixture of a carbonyl source, an ethanolamine-functional compound and an amine-functional compound.

Without being bound to theory this can be summarized in two main reaction steps each composed of multiple sub steps: 1) the activation of the alcohol function (A) by the carbonyl group, the oxazolidinone (B) is assumed to be an intermediate (for the embodiments of this invention mainly in theory, because the carbonyl unit will substantially end up as a cyclic urea unit in the R1 group), 2) the activated alcohol function is replaced by an amine (C) to give a chain extended primary addition product (D). In the presence of ammonia a conversion of the alcohol function to an amine function without giving a chain extension can take place as well. The product (D) may undergo further reaction leading to secondary CO containing products as illustrated by reaction IV and product (F). Such products include but are not limited to cyclic ethylene urea derivatives but include all kinds of CO containing amines as for example illustrated in below examples of CO delivering agents. Optionally the CO groups can be removed leading to the formation of an ethylene amine (E).

The ethanolamine-functional compound is a compound containing one hydroxyl group linked via an ethylene to an amine group that optionally may be present as its carbamate equivalent. Generally the ethanolamine-functional compound is of the following formula

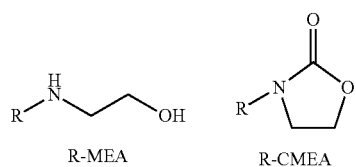

Where R is an ethyleneamine group of the formula $-(C_2H_4-N)_{q-1}-H$ (q being at least 2 as defined above) in which optionally a cyclic urea unit

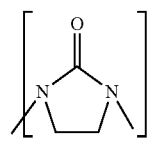

may be present.

Examples of ethanolamine functional compounds include

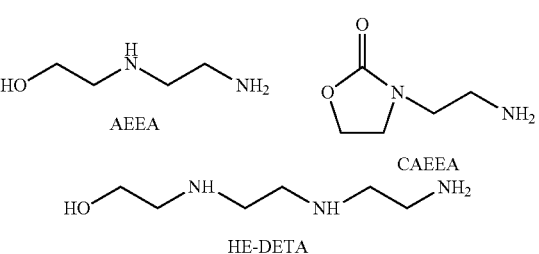

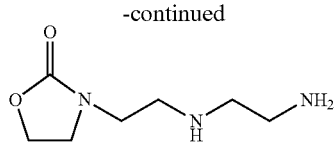

CHE-DETA

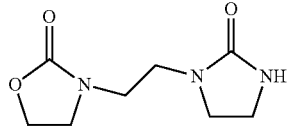

CMEA-UDETA

As to naming convention, AEEA stands for aminoethylethanolamine (also referred to as hydroxyethylethylenediamine), HE-DETA for hydroxyethyldiethylenetriamine, and from there on HE-TETA for hydroxyethyl triethylenetetramine etc. By using the letter C it is indicated that a cyclic carbamate ring is present in the molecule.

The carbon oxide delivering agent is a compound containing a carbonyl moiety that can be transferred to an ethanolamine functional compound leading to the formation of a cyclic carbamate, such as CAEEA (the cyclic carbamate of aminoethyl ethanolamine) or that can be transferred to an ethylene amine (EA) leading to the formation of the corresponding cyclic ethylene urea (UEA). Next to cyclic compounds linear carbamates and ureas may form as well.

Carbon oxide delivering agents within the scope of the present invention include organic compounds in which a carbonyl moiety is available for being transferred as described above. Organic compounds in which a carbonyl moiety is available for being transferred include carbon dioxide, urea, linear and cyclic alkylene ureas, especially cyclic ureas, mono or di-substituted alkylene ureas, alkyl and dialkyl ureas, linear and cyclic carbamates, especially cyclic carbamates, organic carbonates and derivatives or precursors thereof. Such derivatives or precursors may for example include ionic compounds such as carbonate or bicarbonate salts, carbamic acids and associated salts, that can be converted, in some embodiments in situ in the process of the invention, into their non-ionic counterparts, for example into linear and cyclic carbamate or urea compounds. When such ionic compounds are used in the present invention, they are organic hydrocarbon-based carbonate, bicarbonate or carbamate salts. Preferably the CO delivering agent is CO2, urea, or an organic compound wherein alkylene is ethylene, such as a cyclic urea of an ethylene amine, or cyclic carbamate of an ethanolamine, ethylene carbonate, more preferably the carbon oxide delivering agent is at least partly added as carbon dioxide or urea. The carbon oxide delivering agent can be present in the process in the same molecule as the amine functional or the ethanolamine functional compound by using the aforementioned urea or carbamate compounds.

Examples of carbon oxide delivering agents include

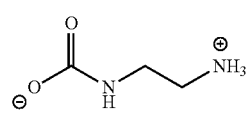

EDA carbamate Zwitterion

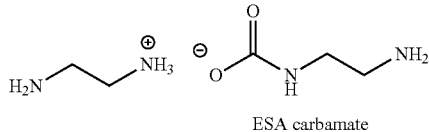

ESA carbamate

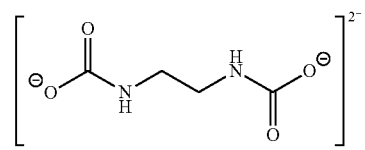

EDA dicarbamate

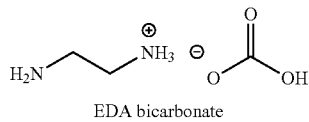

EDA bicarbonate

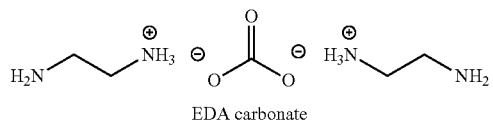

EDA carbonate

DAEC
diaminoethyl carbonate

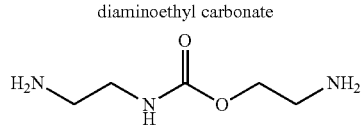

AE AE carbamate

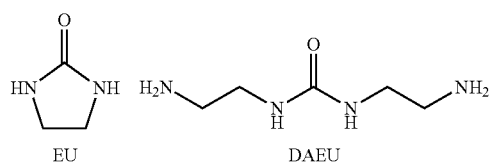

EU          DAEU

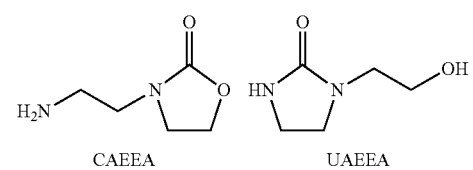

CAEEA          UAEEA

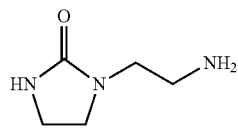

UDETA

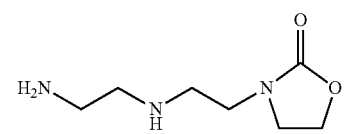

CHE-DETA

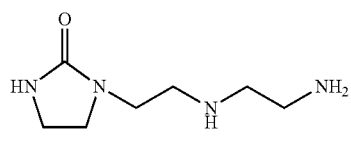

U1TETA

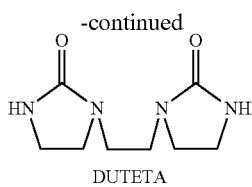

DUTETA

In the above drawing CAEEA again stands for the carbamate of aminoethylethanolamine, UDETA for the urea of diethylene triamine, DAEU stands for diaminoethyl urea, AE AE carbamate stands for amino ethyl aminoethanol carbamate, CHE-DETA stands for the carbamate of hydroxyethyldiethylene triamine, U1TETA stands for the terminal urea of triethylene tetramine, and DUTETA stands for the 1,3-diurea of triethylene tetramine.

The carbon oxide delivering agent is most preferably added to the reaction in the form of carbon dioxide, the carbamate derivative of the ethanolamine-functional compound or the urea derivative of the amine-functional compound, or a combination of these.

Heating a suitable mixture of an ethanolamine, an amine that is not tertiary and a carbon oxide delivering agent to a relatively high temperature provides a way to produce a higher amine and CO containing derivative thereof that can serve as a carbon oxide delivering agent.

The amine-functional compound is a compound containing one or more amine groups, preferably at least two amine groups, and no alcohol groups.

In a preferred embodiment the amine-functional compound is a compound containing at least two amine groups. Even more preferred the amine-functional compound contains at least two primary amine groups, and optionally more amine groups that may be primary, secondary and/or tertiary amines wherein the amine groups within the compound are linked to one another via ethylene groups, and optionally some by a carbonyl moiety (to give a urea unit in the amine functional compound). It should be noted that tertiary amines are only present in an amine of the formula NH2-(C2H4-NH-)pH if there is piperazine unit in the compound.

In another preferred embodiment the ethanolamine-functional compound and the carbon oxide delivering agent are at least partly added as one compound by using a carbamate adduct and/or the amine-functional compound and the carbon oxide delivering agent are at least partly added as one compound by using an urea adduct. A carbamate compound for the present invention is not considered an amine-functional compound, like an ethanolamine-functional compound is not considered an amine-functional compound.

In a more preferred embodiment the ethanolamine-functional compound is AEEA, UAEEA, CAEEA or a mixture thereof and the amine-functional compound EDA, EU or a mixture thereof.

In an embodiment the amine-functional compound and/or the ethanolamine-functional compound are obtained directly or indirectly from an amine production process as described above, such as for example a reductive amination process or EDC process.

For the avoidance of doubt, in the process of the present invention also derivatives of ethylene amines are covered as products, these derivatives are the compounds wherein one or more units —NH—C$_2$H$_4$—NH— may be present as a cyclic ethylene urea unit

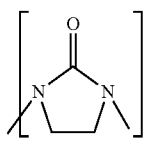

or piperazine unit

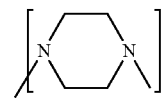

or between two units —NH—C$_2$H$_4$—NH— a carbonyl moiety is present. It should be noted that compounds wherein piperazine units are present are usually only obtained if such piperazine units were also present in one of the reactants. This is not the case for products where a cyclic ethylene urea unit or bridging carbonyl moiety is present, this unit and/or moiety may result from the reaction between any carbon oxide delivering agent and one of an ethanolamine-functional compound, amine-functional compound or obtained ethylene amine product.

The product mixture can be further processed or fractionated into several products that each independently are either pure compounds or mixture of compounds, some of which may be recycled.

The process of the present invention can be done with or without any additional liquid present. If a liquid is added to the reaction system, the liquid preferably is a polar liquid, such as an alcohol or water. Doing the process of the present invention in the presence of water as a liquid or without any additional liquid is preferred.

If any of the ethanolamine-functional compound or amine-functional compound contains piperazine units

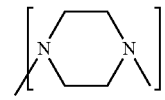

preferably the reaction is performed in a liquid wherein the liquid comprises water as then both the yield and selectivity can be increased. The reactants do not count as part of the above liquid. Hence, even if one or more of the ethanolamine-functional compound, amine-functional compound or carbon oxide delivering agent are liquid at the reaction conditions, these are not considered part of the above liquid in which the process of the invention is performed.

In a preferred embodiment when having compounds with piperazine units in the process of the invention, the liquid contains at least 50 wt-% of water up to 100 wt-% of water, wherein more preferably the remaining up to 50 wt-% is a polar liquid that mixes homogenously with water at the conditions employed during the process of the invention. Even more preferably the liquid contains at least 75 wt-% of water, yet more preferably at least 90 wt-%, most preferably at least 95-wt % on total liquid weight.

The reactor employed can be any suitable reactor including continuously stirred tank reactor, pipeline reactor, tubular or multi-tubular reactor. The reactor may be adiabatic or equipped with external or internal heating devices. Feed may be single point or split into multiple points. It can consist of multiple stages with inter-stage heat exchange.

The process is preferably performed at a temperature of at least 100° C. The temperature should preferably be lower than 400° C. More preferably the temperature is between 200 and 360° C. Even more preferably the temperature is between 230 and 340° C. Most preferably the temperature is between 250 and 310° C.

The reaction time during the process is in an embodiment between 5 minutes and 15 hours, preferably between 10 minutes and 10 hours, more preferably between 15 minutes and 6 hours.

The process can be carried out in one or multiple batch reactors, possibly in fed-batch operation, and/or in a continuously operating system in one reactor or in a cascade of continuous flow reactors, optionally with multiple feeding points. The reaction and separation can be performed in separate steps or at least partially simultaneously. The reaction and separation can involve multiple reaction steps with separation steps in between.

In the large-scale production of chemicals it is preferred to employ a continuous process. The continuous process may be, for example, a single-pass or a recycle process. In a single-pass process, one or more of the reagents pass through the process equipment once, and then the resulting effluent from the reactor is sent for purification or further processing.

The person skilled in the art is capable of selecting the proper reactor and separation unit scheme by determining the overall yield, energy consumption and waste production.

In yet another more preferred embodiment, mixtures of several alcohol and amines can be used that may amongst other contain aminoethylethanolamine (AEEA) and ethylenediamine (EDA), and/or DETA (diethylenetriamine) in combination with further amine-functional compounds and ethanolamine-functional compounds and that are reacted with urea or CO2 as a carbon oxide delivering agent to form higher ethylene polyamines, mainly triethylenetetramine (TETA) and tetraethylenepentamine (TEPA):

EXAMPLES

For a reaction mixture containing a single ethanol amine and its urea derivative in the starting mixture, a general selectivity can be calculated from:

$$\text{Selectivity} = \frac{\text{mol}(U) \text{ ethylene amines formed}}{\text{mol}(U) \text{ ethanolamine at start} - \text{mol}(U) \text{ ethanolamine remaining}}$$

Here, (U)ethylene amine stands for ethylene amine and its urea derivative and (U)ethanol amine stands for ethanol amine and its urea derivative.

For example for the reaction mixture starting with AEEA, EDA and carbon oxide delivering agent, the selectivity is calculated from:

$$\text{Selectivity} = \frac{\text{mol}(D)(U)TETA \text{ formed}}{\text{mol}(U)AEEA \text{ at start} - \text{mol}(U)AEEA \text{ remaining}}$$

Here, (D)(U)TETA stands for tri-ethylene tetra-amine and its mono- and di-urea derivatives and (U)AEEA stands for amino ethyl ethanol amine and its urea derivative.

For a reaction mixture containing more than one ethanol amine and its urea derivative in the starting mixture, a general selectivity can be calculated from:

$$\text{Selectivity} = \frac{\text{mol}(U) \text{ EA formed}}{\text{mol}(U) \text{ ethanolamines at start} - \text{mol}(U) \text{ ethanolamines remaining}}$$

With the ethanolamines and their urea derivatives exclusively the types that were initially present, and not any newly formed (higher) ethanol amines.

Abbreviations Used in Examples

CO=carbon oxide delivering agent
OH=ethanolamine-functional compound
Amine=amine-functional compound
OH/amine is the molar ratio of ethanolamine-functional compound to amine-functional compound
CO/amine is the molar ratio of carbon oxide delivering agent to amine-functional compound
CO/OH is the molar ratio of carbon oxide delivering agent to ethanolamine-functional compound

Example 1

Reaction of UAEEA with EDA and EU. The CO/Amine ratio was varied between 1, 0.6, and 0.2. The OH/amine ratio was kept at 0.3.

The urea derivative of aminoethylethanolamine (UAEEA), ethyleneurea (EU, the urea derivative of ethylenediamine), ethylenediamine (EDA) were added to a microwave vial in the respective amounts as indicated in Table 1. The vials were capped, flushed with $N_2$, and heated at 285° C. for 4 h. The samples were then allowed to cool and the content was analyzed by gas chromatography coupled with a flame ionization detector (GC-FID).

TABLE 1

| Example | 1A | 1B | 1C (comparative) |
|---|---|---|---|
| Reactants | AEEA/EU | AEEA/EU/EDA | AEEA/EU/EDA |
| CO/amine | 1 | 0.6 | 0.2 |
| OH/amine | 0.3 | 0.3 | 0.3 |
| CO/OH | 3.33 | 2 | 0.67 |
| reactant amounts in g | 2.7:7.3 | 2.9:4.8:2.2 | 3.2:1.8:5 |
| molar ratio of reactants | 1:3.33 | 1:2:1.33 | 1:2.67:0.67 |
| Reaction time in hours | 4 | 4 | 4 |
| EDA | 16 | 31 | 46 |
| AEEA | 1 | 2 | 8 |
| EU | 36 | 13 | 3 |
| UAEEA | 16 | 7 | 5 |
| Sum (U)TETA | 25 | 35 | 27 |
| Molar conversion of (U)AEEA | 0.52 | 0.75 | 0.65 |
| Molar selectivity of (U)AEEA to (U)TETA | 0.94 | 0.87 | 0.80 |

All GC FID data in wt. %
Sum (U)TETA denotes the sum of L-TETA and urea adducts thereof In the Table 1 it can be seen that working at the OH/amine ratio of the present invention and a CO/amine ratio that is higher than the OH/amine ratio is favorable for selectivity and also that having the CO/amine at least 50% higher than the OH/amine ratio further improves the selectivity.

Example 2

Reaction of UAEEA with EDA and EU. The CO/Amine ratio was kept at 1. The OH/amine ratio was varied at 0.3, 0.5 and 1.1.

The urea derivative of aminoethylethanolamine (UAEEA), ethyleneurea (EU, the urea derivative of ethylenediamine), ethylenediamine (EDA) were added to a microwave vial in the respective amounts as indicated in Table 2. The vials were capped, flushed with $N_2$, and heated at 285° C. for 4 h. The samples were then allowed to cool and the content was analyzed by gas chromatography coupled with a flame ionization detector (GC-FID).

TABLE 2

| Example | 2A | 2B | 2C (comparative) |
| --- | --- | --- | --- |
| Reactants | AEEA/EU | AEEA/EU | AEEA/EU |
| CO/amine | 1 | 1 | 1 |
| OH/amine | 0.3 | 0.5 | 1.1 |
| CO/amine | 3.33 | 2 | 0.91 |
| reactant amounts in g | 2.7:7.3 | 3.8:6.2 | 5.7:4.3 |
| molar ratio of reactants | 1:3.33 | 1:2 | 1:0.91 |
| Reaction time in hours | 4 | 4 | 4 |
| EDA | 16 | 18 | 14 |
| AEEA | 1 | 2 | 10 |
| EU | 36 | 15 | 3 |
| UAEEA | 16 | 16 | 18 |
| Sum (U)TETA | 25 | 36 | 32 |
| Molar conversion of (U)AEEA | 0.52 | 0.61 | 0.58 |
| Molar selectivity of (U)AEEA to (U)TETA | 0.94 | 0.85 | 0.56 |

All GC FID data in wt. %

Sum (U)TETA denotes the sum of L-TETA and urea adducts thereof

It is clearly demonstrated that the OH/amine ratio has an influence on the molar selectivity towards higher ethylene amines.

Example 3

Reaction of UAEEA with EDA and EU. The CO/OH ratio was varied at 0.75 and 1.5. The OH/amine ratio was varied at 0.5 and 0.6.

The urea derivative of aminoethylethanolamine (UAEEA), ethyleneurea (EU, the urea derivative of ethylenediamine), ethylenediamine (EDA) were added to a microwave vial in the respective amounts as indicated in Table 3. The vials were capped, flushed with $N_2$, and heated at 285° C. for 3.5 h. The samples were then allowed to cool and the content was analyzed by gas chromatography coupled with a flame ionization detector (GC-FID).

TABLE 3

| | Example | | | |
| --- | --- | --- | --- | --- |
| | 3A | 3B | 3C (comparative) | 3D (comparative) |
| reactants | AEEA/UAEEA/EU/EDA | AEEA/UAEEA/EU/EDA | AEEA/EU/EDA | AEEA/EU/EDA |
| CO/amine | 0.75 | 0.9 | 0.375 | 0.45 |
| OH/amine | 0.5 | 0.6 | 0.5 | 0.6 |
| CO/OH | 1.5 | 1.5 | 0.75 | 0.75 |
| reactant amounts in g | 2.57:1.68:3.88:1.86 | 2.85:1.78:4.13:1.24 | 4.27:2.65:3.08 | 4.65:2.28:2.47 |
| molar ratio of reactants | 1:0.5:1.75:1.25 | 1:0.5:1.75:0.75 | 1:0.75:1.25 | 1:0.75:0.92 |
| Reaction time in hours | 3.5 | 3.5 | 3.5 | 3.5 |
| EDA | 23 | 17 | 40 | 35 |
| AEEA | 3 | 3 | 14 | 13 |
| EU | 13 | 11 | 5 | 4 |
| UAEEA | 14 | 17 | 17 | 18 |
| Sum (U)TETA | 28 | 30 | 11 | 12 |
| Molar conversion of (U)AEEA | 0.63 | 0.62 | 0.36 | 0.41 |
| Molar selectivity of (U)AEEA to (U)TETA | 0.64 | 0.65 | 0.44 | 0.39 |

All GC FID data in wt. %

Sum (U)TETA denotes the sum of L-TETA and urea adducts thereof

Table 3 demonstrates that when having the OH/amine ratio between 0.05:1 and 0.7:1, selectivity improves when the CO:amine ratio is higher than the OH:amine ratio. The yield of the desired (U)TETA product is much higher when operating at this higher CO/amine ratio. Experiments 3A and 3B have a much higher yield and selectivity towards (U)TETA's as compared to experiments 3C and 3D.

Example 4

Reaction of UAEEA with EDA and EU CO/Amine=0.875 and OH/amine=0.25

The urea derivative of aminoethylethanolamine (UAEEA), ethyleneurea (EU, the urea derivative of ethylenediamine), ethylenediamine (EDA) were added to a microwave vial in the respective amounts as indicated in Table 4. The vials were capped, flushed with N2, and heated at 280° C. for 2.5 and 5 h, respectively. The samples were then allowed to cool and the content was analyzed by gas chromatography coupled with a flame ionization detector (GC-FID).

TABLE 4

| Example | 4a | 4b |
| --- | --- | --- |
| reactants | UAEEA/EU/EDA | UAEEA/EU/EDA |
| CO/amine | 0.875 | 0.875 |
| OH/amine | 0.25 | 0.25 |
| CO/OH | 3.5 | 3.5 |
| reactant amounts in g | 0.45/0.775/0.311 | 0.45/0.775/0.311 |
| molar ratio of reactants | 1:2.5:1.5 | 1:2.5:1.5 |
| Reaction time in hours | 2.5 | 5 |
| EDA | 17.3 | 17.2 |
| AEEA | 0.7 | 0.4 |
| EU | 36.1 | 32.1 |
| UAEEA | 14.2 | 8.1 |
| Sum (U)TETA | 20.1 | 27.3 |
| Molar conversion of (U)AEEA | 0.49 | 0.71 |
| Molar selectivity of (U)AEEA to (U)TETA | 0.99 | 0.98 |

All GC FID data in wt. %
Sum (U)TETA denotes the sum of L-TETA and urea adducts thereof Molar selectivities above 0.95 were achieved by using a reaction mixture where the ratio ethanolamine-functional compound:amine-functional compound is in the range of the invention and the carbon oxide delivering agent is dosed in a higher amount on amine-functional compound than the ethanolamine compound is dosed on the amine-functional compound.

Example 5

Reaction of UAEEA with EDA and EU CO/amine=1.07 and OH/amine=0.33

The urea derivative of aminoethylethanolamine (UAEEA), ethyleneurea (EU, the urea derivative of ethylenediamine), ethylenediamine (EDA) were added to a microwave vial in the respective amounts as indicated in Table 5. The vials were capped, flushed with $N_2$, and heated at 280° C. for 5 and 10 h, respectively. The samples were then allowed to cool and the content was analyzed by GC-FID.

TABLE 5

| Example | 5a | 5b |
| --- | --- | --- |
| reactants | UAEEA/EU/EDA | UAEEA/EU/EDA |
| CO/amine | 1.07 | 1.07 |
| OH/amine | 0.33 | 0.33 |
| CO/OH | 3.2 | 3.2 |
| reactant amounts in g | 0.45/0.682/0.166 | 0.45/0.682/0.166 |
| molar ratio of reactants | 1:2.2:0.8 | 1:2.2:0.8 |
| Reaction time in hours | 5 | 10 |
| EDA | 12.9 | 11.8 |
| AEEA | 0.3 | n.d. |
| EU | 31.1 | 25.6 |
| UAEEA | 12.1 | 3.9 |
| Sum (U)TETA | 25.9 | 32.5 |
| Molar conversion of (U)AEEA | 0.64 | 0.89 |
| Molar selectivity of (U)AEEA to (U)TETA | 0.88 | 0.81 |

All GC-FID data in wt. %
Sum (U)TETA denotes the sum of L-TETA and urea adducts thereof Molar selectivities above 0.8 were achieved by using a reaction mixture where the ratio ethanolamine-functional compound:amine-functional compound is relatively low and the carbon oxide delivering agent is dosed in a higher amount on amine-functional compound than the ethanolamine compound is dosed on the amine-functional compound. Comparison with Example 4 shows that both the CO/Amine and OH/amine ratio's are relevant for obtaining high selectivities.

Comparative Example 6

Reaction of AEEA with EDA and EU CO/amine=0.75 and OH/amine=1

The aminoethylethanolamine (AEEA), ethyleneurea (EU, the urea derivative of ethylenediamine), ethylenediamine (EDA) were added to a pressure vessel in the respective amounts as indicated in Table 6. The reaction vessel was closed, flushed with $N_2$ and heated to 270° C. for 5 h. The sample was then allowed to cool and the content was analyzed by GC-FID.

TABLE 6

| Example | 6 |
| --- | --- |
| reactants | AEEA/EU/EDA |
| CO/amine | 0.75 |
| OH/amine | 1 |
| CO/OH | 0.75 |
| reactant amounts in g | 10/6.2/1.44 |
| molar ratio of reactants | 1:0.75:0.25 |
| Reaction time in hours | 2.5 |
| EDA | 15.5 |
| AEEA | 8.7 |
| EU | 3.3 |
| UAEEA | 12.7 |
| Sum (U)TETA | 28.1 |
| Molar conversion of (U)AEEA | 0.67 |
| Molar selectivity of (U)AEEA to (U)TETA | 0.45 |

All GC-FID data in wt. %
Sum (U)TETA denotes the sum of L-TETA and urea adducts thereof Conclusion: Molar selectivities of 0.45 were achieved by using a reaction mixture where the ratio ethanolamine-functional compound:amine-functional compound is outside the range of the invention and higher than the carbon oxide delivering agent:amine-functional compound ratio. The Example clearly shows that the selectivity of AEEA towards L-TETA and urea adducts thereof is much lower than for the Examples where the carbon oxide delivering agent:amine functional compound ratio is higher than the ethanolamine-function compound:amine-functional compound ratio.

Example 7 Reaction of UAEEA with DETA and UDETA CO/amine=1 and 1.33, OH/amine=0.33

The urea derivative of aminoethylethanolamine (UAEEA) and the urea derivative of diethylenetriamine (UDETA) and diethylenetriamine (DETA) were added to a pressure vessel in the respective amounts as indicated in Table 7. The pressure vessel was closed, flushed with $N_2$, and heated at for 4 h at the reaction temperature as shown in Table 7. The sample was then allowed to cool and the content was analyzed by GC-FID.

TABLE 7

| Example | 7a | 7b |
| --- | --- | --- |
| reactants | UAEEA/UDETA/DETA | UAEEA/UDETA |
| CO/amine | 1 | 1.33 |

TABLE 7-continued

| Example | 7a | 7b |
|---|---|---|
| OH/amine | 0.33 | 0.33 |
| CO/OH | 3 | 4 |
| reactant amounts in g | 5.0/10.35/3.88 | 5.0/15.5 |
| reaction temperature | 280° C. | 290° C. |
| molar ratio of reactants | 1:2:1 | 1:3 |
| Reaction time in hours | 4 h | 4 h |
| DETA | 10.7 | 0.3 |
| AEEA | 2.9 | 1.7 |
| UDETA | 56.6 | 58.9 |
| UAEEA | 8.1 | 6.6 |
| Sum (U)TEPA | 15.4 | 21.9 |
| Molar conversion of (U)AEEA | 0.56 | 0.72 |
| Molar selectivity of (U)AEEA to (U)TEPA | 0.60 | 0.66 |

All GC-FID data in wt. %
Sum (U)TEPA denotes the sum of L-TEPA and urea adducts thereof Conclusion: molar selectivities of above 0.6 were achieved by using a reaction mixture where the ratio ethanolamine-functional compound:amine-functional compound is in the range of the invention and the carbon oxide delivering agent is dosed in a higher amount on amine-functional compound than the ethanolamine compound is dosed on the amine-functional compound.

The product mixture obtained in Example 7b was treated with a sodium hydroxide solution after which the amount of TEPA (i.e. tetraethylenepentamine without cyclic ethylene urea unit) on total (U)TEPA was increased.

Comparative Example 8

Reaction of UAEEA with DETA CO/amine=1, OH/amine=1

The urea derivative of aminoethylethanolamine (UAEEA) and diethylenetriamine (DETA) were added to a pressure vessel in the respective amounts as indicated in Table 8. The pressure vessel was closed, flushed with $N_2$, and heated at 270° C. for 5 h. The sample was then allowed to cool and the content was analyzed by GC-FID.

TABLE 8

| Example | 8 |
|---|---|
| reactants | UAEEA/DETA |
| CO/amine | 1 |
| OH/amine | 1 |
| CO/OH | 1 |
| reactant amounts in g | 10/7.9 |
| molar ratio of reactants | 1/1 |
| Reaction time in hours | 5 h |
| DETA | 13.8 |
| AEEA | 16.8 |
| UDETA | 30.5 |
| UAEEA | 16.0 |
| Sum (U)TEPA | 5.4 |
| Molar conversion of (U)AEEA | 0.34 |
| Molar selectivity of (U)AEEA to (U)TEPA | 0.10 |

All GC-FID data in wt. %
Sum (U)TEPA denotes the sum of L-TEPA and urea adducts thereof A molar selectivity of only 0.1 was achieved by using a reaction mixture where the ratio ethanolamine-functional compound:amine-functional compound is higher than 0.7:1 and moreover equal to the carbon oxide delivering agent:amine-functional compound ratio. The example clearly shows that the selectivity of AEEA towards L-TEPA and urea adducts thereof is much lower than in previous example where the carbon oxide delivering agent:amine functional compound ratio is higher than the ethanolamine-function compound:amine-functional compound ratio.

Example 9

Reaction of AEEA with EDA in the presence of CO2. CO/amine=1 and OH/amine=0.5

The aminoethylethanolamine (AEEA), ethylenediamine (EDA) and carbon dioxide gas (CO2) were added to a high pressure autoclave in the respective amounts as indicated in Table 9. Before addition of the $CO_2$, the autoclaves were filled with the EDA and AEEA, flushed with $N_2$. The $CO_2$ was added after pre-heating the amine mixture to a temperature of 130° C. The mixture was heated to 280° C. with a heating rate of 5° C./min. After reaching a temperature of 280° C., the reaction mixture was kept at the setpoint temperature for 2 h and 4.5 h, respectively. The samples were then allowed to cool and the content was analyzed by GC-FID.

TABLE 9

| Example | 9a | 9b |
|---|---|---|
| reactants | AEEA/EDA/CO2 | AEEA/EDA/CO2 |
| CO/amine | 1 | 1 |
| OH/amine | 0.5 | 0.5 |
| CO/OH | 2 | 2 |
| reactant amounts in g | 33.3/38.5/28.5 | 33.3/38.5/28.5 |
| molar ratio of reactants | 1:2:2 | 1:2:2 |
| Reaction time in hours | 2 h | 4.5 h |
| EDA | 21.7 | 17.9 |
| AEEA | 6.2 | 4.6 |
| EU | 9.8 | 7.0 |
| UAEEA | 22.9 | 14.0 |
| Sum (U)TETA | 12.9 | 23.2 |
| Molar conversion of (U)AEEA | 0.28 | 0.53 |
| Molar selectivity of (U)AEEA to (U)TETA | 0.76 | 0.72 |

All GC-FID data in wt. %
Sum (U)TETA denotes the sum of L-TETA and urea adducts thereof Conclusion: molar selectivities of above 0.7 were achieved by using a reaction mixture where the ratio ethanolamine-functional compound:amine-functional compound is in the claimed range, the carbon oxide delivering agent is dosed as CO2 in the gas phase and is dosed in a higher amount on amine-functional compound than the ethanolamine compound is dosed on the amine-functional compound.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. A process to prepare ethyleneamines of the formula $NH_2-(C_2H_4-NH-)_pH$ wherein p is at least 3, or derivatives thereof wherein one or more units $-NH-C_2H_4-NH-$ may be present as a cyclic ethylene urea unit

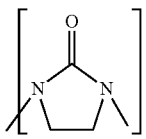

or piperazine unit

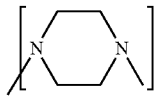

or between two units $-NH-C_2H_4-NH-$ a carbonyl moiety is present, the process comprising:
reacting an ethanolamine-functional compound $HO-(C_2H_4-NH-)_qH$ wherein q is at least 2, an amine-functional compound $NH_2-(C_2H_4-NH-)_rH$ wherein r is at least 1, in the presence of a carbon oxide delivering agent, wherein the molar ratio of ethanolamine-functional compound to amine-functional compound is from 0.05:1 to 0.7:1 and the molar ratio of carbon oxide delivering agent to amine-functional compound is higher than the molar ratio of ethanolamine-functional compound to amine-functional compound, provided that the process does not comprise reacting 3 moles of ethylenediamine (EDA) and 1 mole of AEEA (aminoethylethanolamine) in the presence of 1.65 moles of urea at 280 deg C. for 2 hours.

2. The process of claim 1 wherein the molar ratio of carbon oxide delivering agent to amine-functional compound is at least 10% higher than the molar ratio of ethanolamine-functional compound to amine-functional compound.

3. The process of claim 1 wherein the molar ratio of carbon oxide delivering agent to amine-functional compound is at least 50% higher than the molar ratio of ethanolamine-functional compound to amine-functional compound.

4. The process of claim 1 wherein the molar ratio of carbon oxide delivering agent to amine-functional compound is up to 500% higher than the molar ratio of ethanolamine-functional compound to amine-functional compound.

5. A process to prepare ethyleneamines of the formula $NH_2-(C_2H_4-NH-)_pH$ wherein p is at least 3, or derivatives thereof wherein one or more units $-NH-C_2H_4-NH-$ may be present as a cyclic ethylene urea unit

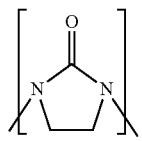

or piperazine unit

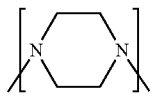

or between two units $NH-C_2H_4-NH-$ a carbonyl moiety is present, the process comprising:
reacting an ethanolamine-functional compound $HO-(C2H_4-NH-)_qH$ wherein q is at least 2, an amine-functional compound $NH_2-(C_2H_4-NH-)_rH$ wherein r is at least 1, in the presence of a carbon oxide delivering agent, wherein the molar ratio of ethanolamine-functional compound to amine-functional compound is from 0.1 to 0.5 and the molar ratio of carbon oxide delivering agent to amine-functional compound is higher than the molar ratio of ethanolamine-functional compound to amine-functional compound, provided that the process does not comprise reacting 3 moles of ethylenediamine (EDA) and 1 mole of AEEA (aminoethylethanolamine) in the presence of 1.65 moles of urea at 280 deg C. for 2 hours.

6. The process of claim 1 further comprising providing a carbamate adduct to the reaction of the ethanolamine-functional compound, the amine-functional compound, and the carbon oxide delivering agent.

7. The process of claim 1 further comprising providing an urea adduct to the reaction of the ethanolamine-functional compound, the amine-functional compound, and the carbon oxide delivering agent.

8. The process of claim 1 further comprising converting the obtained cyclic ethylene urea into its corresponding ethylene amine.

9. The process of claim 1 wherein the ethanolamine-functional compound is AEEA (aminoethylethanolamine), CAEEA (the carbamate of aminoethylethanolamine), UAEEA (the urea of aminoethylethanolamine) or a mixture thereof and the amine-functional compound is EDA (ethylenediamine), EU, (ethyleneurea) or a mixture thereof.

10. The process of claim 1 wherein the ethanolamine-functional compound is AEEA (aminoethylethanolamine), CAEEA (the carbamate of aminoethylethanolamine), UAEEA (the urea of aminoethylethanolamine) or a mixture thereof and the amine-functional compound is DETA (diethylenetriamine), UDETA, (the urea of DETA) or a mixture thereof.

11. The process of claim 5 wherein the molar ratio of carbon oxide delivering agent to amine-functional compound is at least 10% higher than the molar ratio of ethanolamine-functional compound to amine-functional compound.

12. The process of claim 5 wherein the molar ratio of carbon oxide delivering agent to amine-functional compound is at least 50% higher than the molar ratio of ethanolamine-functional compound to amine-functional compound.

13. The process of claim 5 wherein the molar ratio of carbon oxide delivering agent to amine-functional compound is up to 500% higher than the molar ratio of ethanolamine-functional compound to amine-functional compound.

14. The process of claim 5 further comprising providing a carbamate adduct to the reaction of the ethanolamine-functional compound, the amine-functional compound, and the carbon oxide delivering agent.

15. The process of claim 5 further comprising providing a urea adduct to the reaction of the ethanolamine-functional compound, the amine-functional compound, and the carbon oxide delivering agent.

16. The process of claim 5 further comprising converting the obtained cyclic ethylene urea into its corresponding ethylene amine.

17. The process of claim 5 wherein the ethanolamine-functional compound is AEEA (aminoethylethanolamine), CAEEA (the carbamate of aminoethylethanolamine), UAEEA (the urea of aminoethylethanolamine) or a mixture thereof and the amine-functional compound is EDA (ethylenediamine), EU, (ethyleneurea) or a mixture thereof.

18. The process of claim 5 wherein the ethanolamine-functional compound is AEEA (aminoethylethanolamine), CAEEA (the carbamate of aminoethylethanolamine), UAEEA (the urea of aminoethylethanolamine) or a mixture thereof and the amine-functional compound is DETA (diethylenetriamine), UDETA, (the urea of DETA) or a mixture thereof.

* * * * *